(12) United States Patent
Liu et al.

(10) Patent No.: US 9,958,663 B2
(45) Date of Patent: May 1, 2018

(54) LIGHT-TRAPPING CANCER CELL STAGE TESTING METHOD

(71) Applicant: National Kaohsiung University of Applied Sciences, Kaohsiung (TW)

(72) Inventors: Shih-Kun Liu, Kaohsiung (TW); Li-Chin Chen, Kaohsiung (TW); Chia-Ching Tsai, Kaohsiung (TW); Wen-Kai Hsieh, Kaohsiung (TW); Fong-Min Hsu, Kaohsiung (TW); Yong-Jai Shen, Kaohsiung (TW); Wei-Yi Sung, Kaohsiung (TW)

(73) Assignee: National Kaohsiung University of Applied Sciences, Kaohsiung (TW)

( * ) Notice: Subject to any disclaimer, the term of this patent is extended or adjusted under 35 U.S.C. 154(b) by 20 days.

(21) Appl. No.: 15/235,159

(22) Filed: Aug. 12, 2016

(65) Prior Publication Data

US 2017/0108687 A1    Apr. 20, 2017

(30) Foreign Application Priority Data

Oct. 19, 2015   (TW) .............................. 104134157 A

(51) Int. Cl.
```
G02B 21/32      (2006.01)
G01N 33/483     (2006.01)
G01N 15/14      (2006.01)
G21K 1/00       (2006.01)
G01N 15/10      (2006.01)
```

(52) U.S. Cl.
CPC .............. *G02B 21/32* (2013.01); *G01N 15/14* (2013.01); *G01N 33/4833* (2013.01); *G21K 1/00* (2013.01); *G01N 2015/1006* (2013.01); *G01N 2015/1075* (2013.01)

(58) Field of Classification Search
CPC ...................................................... G02B 21/32
See application file for complete search history.

(56) References Cited

FOREIGN PATENT DOCUMENTS

| TW | I241421 B | 10/2005 |
| TW | I474061 B | 2/2015 |

OTHER PUBLICATIONS

Wang et al. Lab Chip, 2011, 11:3656-3662.*

* cited by examiner

*Primary Examiner* — Bin Shen
(74) *Attorney, Agent, or Firm* — Alan D. Kamrath; Kamrath IP Lawfirm, P.A.

(57) ABSTRACT

A light-trapping cancer cell stage testing method includes: measuring a first average escape velocity or range of first cancer cells and a second average escape velocity or range of second cancer cells whose stage is known and differ from that of the first cancer cells and whose types are known; utilizing the first average escape velocity and the second average escape velocity to calculate a reference ratio to build a database; selecting stage-unknown cancer cells and measuring an escape velocity of the stage-unknown cancer cells (type-known); utilizing the escape velocity of the stage-unknown cancer cells and an escape velocity of reference-stage cancer cells to calculate a ratio; and determining a stage of the stage-unknown cancer cells with a result comparing the ratio of the escape velocities for the stage-unknown cancer cells with the reference ratios stored in the database.

20 Claims, 9 Drawing Sheets

Bladder Cancer Cell

TSGH-8301
second stage

T24
third stage

LIGHT-TRAPPING CANCER CELL STAGE TESTING METHOD

BACKGROUND OF THE INVENTION

1. Field of the Invention

The present invention relates to a light-trapping cancer cell stage testing method. Particularly, the present invention relates to the laser-beam light-trapping cancer cell stage testing method. More particularly, the present invention relates to the light-trapping cancer cell stage testing method utilizing an optical fiber tweezer. More particularly, the present invention relates to the laser light-trapping cancer cell stage testing method utilizing a laser fiber optical tweezer.

2. Description of the Related Art

Taiwanese patent publication No. 1241421, entitled "Method for Fabricating Hyperbolic Shape Fiber Lens," discloses a method comprising: (a) stripping a predetermined length of a coating layer of a fiber to form a bare fiber portion; (b) cleaning the bare fiber portion; (c) fixing the fiber in a fiber holder; (d) providing a container with a hydrofloride layer, an oil layer and a mixed layer; (e) immersing the bare fiber portion in the container, wherein the bare fiber portion is etched by the layer of hydrofloride and the fiber is perpendicular to the surface of the layer of oil to form a cone; (f) melting the cone by a plurality of electric arcs to form a fiber lens; and (g) adjusting a relative position between the electric arcs and the cone to form a hyperbolic shape fiber lens and a desired curvature according to an uneven temperature field.

However, the method, disclosed in Taiwanese patent publication No. 1241421, is merely suitable for mass production of the fiber lens. Furthermore, the above-mentioned method also discloses the relative position for matching the electric arcs and the cone to obtain the desired curvature of the hyperbolic shape fiber lens for enhancing efficiency of optical coupling.

Another Taiwanese patent publication No. 1474061, entitled "Manufacturing Method for Fiber Optical Tweezers," discloses a method comprising: (a) peeling step: cutting a predetermined distance of an optical fiber and stripping off a coating of the optical fiber to expose a bare portion of the optical fiber, including a cladding layer and a fiber core; (b) cleaning step: cleaning the bare portion of the optical fiber; (c) cutting step: cutting an end surface of the bare portion to form a flat end surface; (d) etching step: fixing the optical fiber to immerse the bare portion in a buffer oxide etch (BOE) solution contained a container to etch the bare portion to form a cone-shaped end portion of a fiber microlens. Furthermore, the method comprises shaping step: melting the cone-shaped end portion of a fiber microlens with electric arcs generated by a two-terminal device to form a hemisphere-shaped end portion of the fiber microlens.

Advantageously, the manufacturing method of the hemisphere-shaped end portion of the fiber microlens as a key component, disclosed in Taiwanese patent publication No. 1474061, simplifies the entire process and reduces the total manufacturing cost. In biomedicine application, the optical fiber tweezer is utilized to operationally emit light to catch tiny objects in a non-contact manner with high efficiency and low power consumption.

As mentioned above, the optical fiber tweezer is merely suitable for trapping (catching) tiny objects in a non-contact manner. Furthermore, the non-contact trapping characteristic of the optical fiber tweezer must be also suitable for other biomedicine applications or the likes in the future. However, there is a need of improving and broadening the use of the optical fiber tweezer. The above-mentioned patent publications are incorporated herein by reference for purposes including, but not limited to, indicating the background of the present invention and illustrating the situation of the art.

As is described in greater detail below, the present invention provides a light-trapping cancer cell stage testing method. An optical fiber tweezer is operated to measure escape velocities (or velocity ranges) of first cancer cells and second cancer cells whose types and stages are known. Average escape velocities (or velocity ranges) of different cancel cell stages is calculated to construct an identification standard database for the same type of the cancer cells. Accordingly, the average escape velocities (or velocity ranges) can be utilized to identify an unknown stage of the same cancer cell type in such a way as to improve the conventional cancer cell stage testing method.

SUMMARY OF THE INVENTION

The primary objective of this invention is to provide a light-trapping cancer cell stage testing method. An optical fiber tweezer is operated to measure escape velocities (or velocity ranges) of first cancer cells and second cancer cells whose types and stages are known. Average escape velocities (or velocity ranges) of different cancel cell stages is calculated to construct an identification standard database for same type of the cancer cells. The average escape velocities can be utilized to identify an unknown stage of the same cancer cell type. Advantageously, the cancer cell stage testing method of the present invention is successful in testing the unknown stage of the cancer cells.

The light-trapping cancer cell stage testing method in accordance with an aspect of the present invention includes:

utilizing an optical fiber tweezer to measure escape velocities (or velocity ranges) of first cancer cells and second cancer cells whose types are the same, with selecting the first cancer cells and the second cancer cells from different stages;

calculating average escape velocities (or velocity ranges) of the first cancer cells and the second cancer cells by a statistical method;

measuring at least one escape velocity (or velocity range) of stage-unknown, type-known cancer cells by the optical fiber tweezer;

comparing the escape velocity (or velocity range) of the stage-unknown, type-known cancer cells with the average escape velocities (or velocity ranges) of the first cancer cells and the second cancer cells to obtain a result; and identifying a stage of the stage-unknown, type-known cancer cells according to the result.

In a separate aspect of the present invention, the first cancer cells and the second cancer cells are various human cancer cells for cancer cell identification.

In a further separate aspect of the present invention, the escape velocities (or velocity ranges) of the first cancer cells and the second cancer cells are collected to construct an identification standard database.

In yet a further separate aspect of the present invention, the escape velocities (or velocity ranges) of the first cancer cells and the second cancer cells include maximum escape velocities (or velocity ranges) and minimum escape velocities (or velocity ranges).

In yet a further separate aspect of the present invention, the average escape velocities (or velocity ranges) of the first cancer cells and the second cancer cells are calculated from pathological first-stage escape velocities (or velocity ranges), pathological second-stage escape velocities (or velocity ranges), pathological third-stage escape velocities (or velocity ranges) or pathological fourth-stage escape velocities (or velocity ranges).

In yet a further separate aspect of the present invention, the escape velocities (or velocity ranges) of the first cancer cells and the second cancer cells are calculated to provide a reference ratio of escape velocity or cell-trapping efficiency.

In yet a further separate aspect of the present invention, the escape velocity of the stage-unknown, type-known cancer cells includes a maximum escape velocity (or velocity range) and a minimum escape velocity (or velocity range).

In yet a further separate aspect of the present invention, the stage-unknown, type-known cancer cells are human bladder cancer cells.

In yet a further separate aspect of the present invention, the stage-unknown, type-known cancer cells are human colon cancer cells.

In yet a further separate aspect of the present invention, the optical fiber tweezer is a laser optical fiber tweezer. In yet a further separate aspect of the present invention, the optical fiber tweezer has a cell-trapping obliquity or a working distance for cancer cell trapping operation and the cell-trapping obliquity is at 50 degrees.

In yet a further separate aspect of the present invention, the optical fiber tweezer includes a single-mode optical fiber or a single-mode optical fiber microlens.

Further scope of the applicability of the present invention will become apparent from the detailed description given hereinafter. However, it should be understood that the detailed description and specific examples, while indicating preferred embodiments of the invention, are given by way of illustration only, since various will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1:
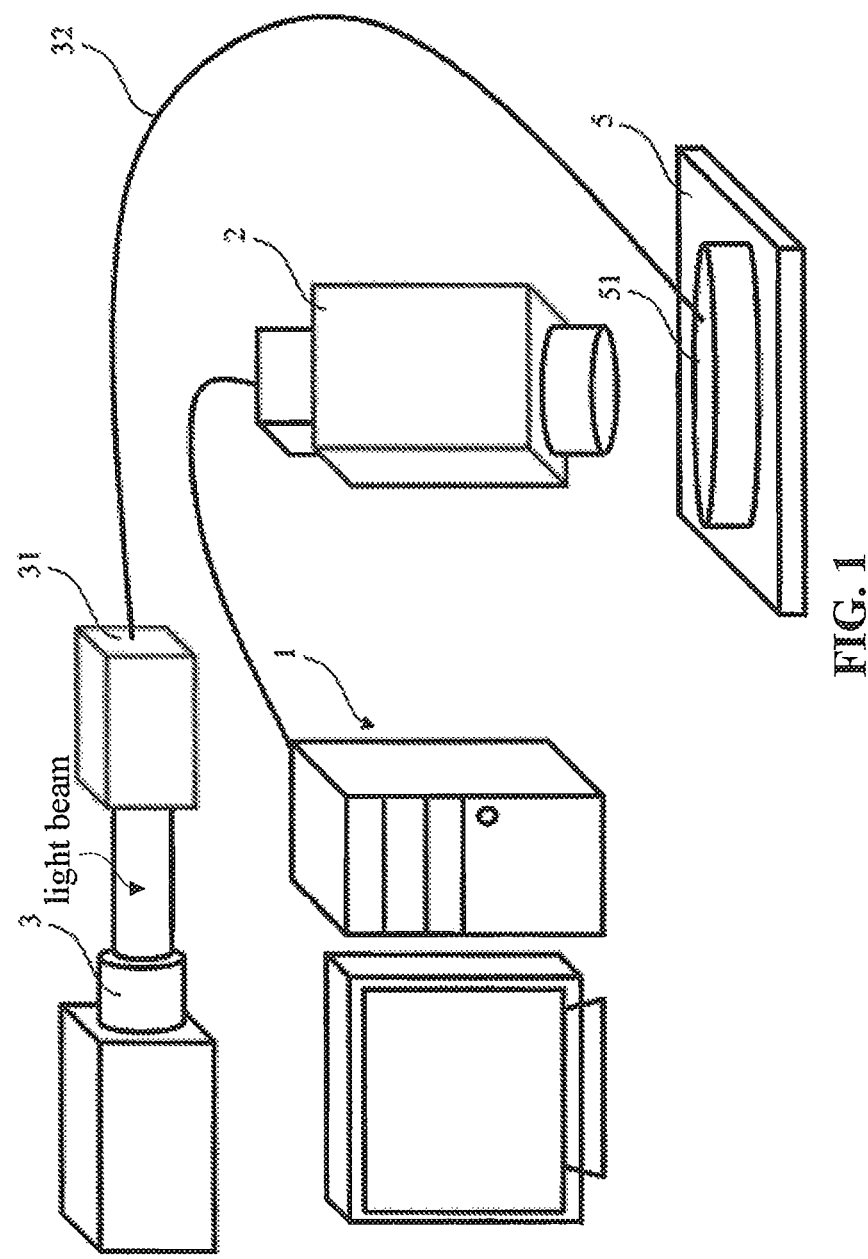
FIG. 1 is a schematic view of an optical fiber tweezer system applied to process a light-trapping cancer cell stage testing method in accordance with a preferred embodiment of the present invention.

The term "cancer cell stage" used herein defines a degree of staging of origination and spread of cancer diseases. Generally, the tumor node metastasis (TNM) classification is a globally recognized standard that provides codes to describe the stage of a person's cancer. The TNM classification is developed by the Union for International Cancer Control (UICC) and is also used by the American Joint Committee on Cancer (AJCC). In the TNM classification, T category describes the size of the original (primary) tumor site and whether it has invaded nearby tissue, N category describes nearby (regional) lymph node involvement and M category describes distant metastatic spread.

According to the TNM classification, it generally provides stage I, stage II, stage III and stage IV. In stage I, cancers are localized to one part of the body. In stages II and III, cancers are locally advanced. In stage IV, cancers have often metastasized, or spread to other organs or throughout the body. The classification of cancer by anatomic extent of disease, i.e. stage, is the major determinant of appropriate treatment and prognosis. Stage is an increasingly important component of cancer surveillance, cancer treatment, follow-up care after treatment, cancer control and an endpoint for the evaluation of the population-based screening and early detection efforts.

It is noted that a light-trapping cancer cell stage testing method in accordance with the preferred embodiment of the present invention can be applicable to stage various cancers, including bladder cancer, colon cancer or other cancer for example. Furthermore, the light-trapping cancer cell stage testing method in accordance with the preferred embodiment of the present invention is suitable for various wavelengths of light or laser (e.g., ultra-violet laser, violet laser, blue laser, green laser, red laser or infrared laser), which are not limitative of the present invention.

In a preferred embodiment, the light-trapping cancer cell stage testing method of the present invention presets parameters of an optical fiber tweezer system which is operated to experimentally measure escape velocities and diameters of given cancer cells whose type and stage is known or identified. An average escape velocity or an escape velocity range of the known cancer cells is calculated by a statistical method. Further, a reference ratio or a reference ratio range of the average escape velocity or the escape velocity range of the known cancer cells is calculated to construct an identification standard database. In cancer cell stage testing operation, the optical fiber tweezer system is operated to measure escape velocities and diameters of stage-unknown cancer cells whose type are known, and an ratio or a ratio range of escape velocity or cell-trapping efficiency is further calculated. Next, the ratio of escape velocity or cell-trapping efficiency of the stage-unknown cancer cells is compared with that of the same-type, stage-known cancer cell stored in the identification standard database.

FIG. 1 shows a schematic view of an optical fiber tweezer system applied to process a light-trapping cancer cell stage testing method in accordance with a preferred embodiment of the present invention. Turning now to FIG. 1, by way of example, the optical fiber tweezer system includes a computer system 1, a microscope system 2, a laser source device 3 and a working platform (or operational platform) 5 which are suitably connected.

With continued reference to FIG. 1, by way of example, the computer system 1 includes a computer device, a display device and other peripherals (not shown). The computer device connects with the microscope system 2 while the computer system 1 is provided at a predetermined position. Furthermore, the computer system 1 selectively connects with the laser source device 3 or the working platform 5.

With continued reference to FIG. 1, by way of example, the microscope system 2 includes a charge coupled device (CCD) component, two microscopic lens systems (e.g. eyepiece lens and objective lenses), a set of light sources, several optical filters, and other functional device (e.g., fixing device). In assembling, the CCD component is mounted on the microscope device and is operated to capture at least one or a series of microscopic images. In testing operation, the microscope system 2 is positioned at a predetermined position above the working platform 5 for capturing microscopic images.

With continued reference to FIG. 1, by way of example, the laser source device 3 is selected from a 980 nm laser source and includes a laser source, a fiber coupling device 31 and an optical fiber mircrolens 32. The laser source connects with the optical fiber mircrolens 32 via the fiber coupling device 31. A laser beam is excited and is emitted from the laser source via the optical fiber mircrolens 32 to form a laser optical fiber tweezer. In cancer cell stage testing, the laser optical fiber tweezer is operated to execute a procedure of trapping cancer cells.

With continued reference to FIG. 1, by way of example, the working platform 5 is selected from an X-Y electrical control table (or plate) or other automatic and electrical control table which can be automatically and electrically controlled. A fluid containing stage-unknown cancer cells is contained in a vessel 51 or the like (e.g., Petri dish) on the working platform 5, which has an adjustable horizontal plane that is controllably adjusted its angle for testing operation.

Figure 2:
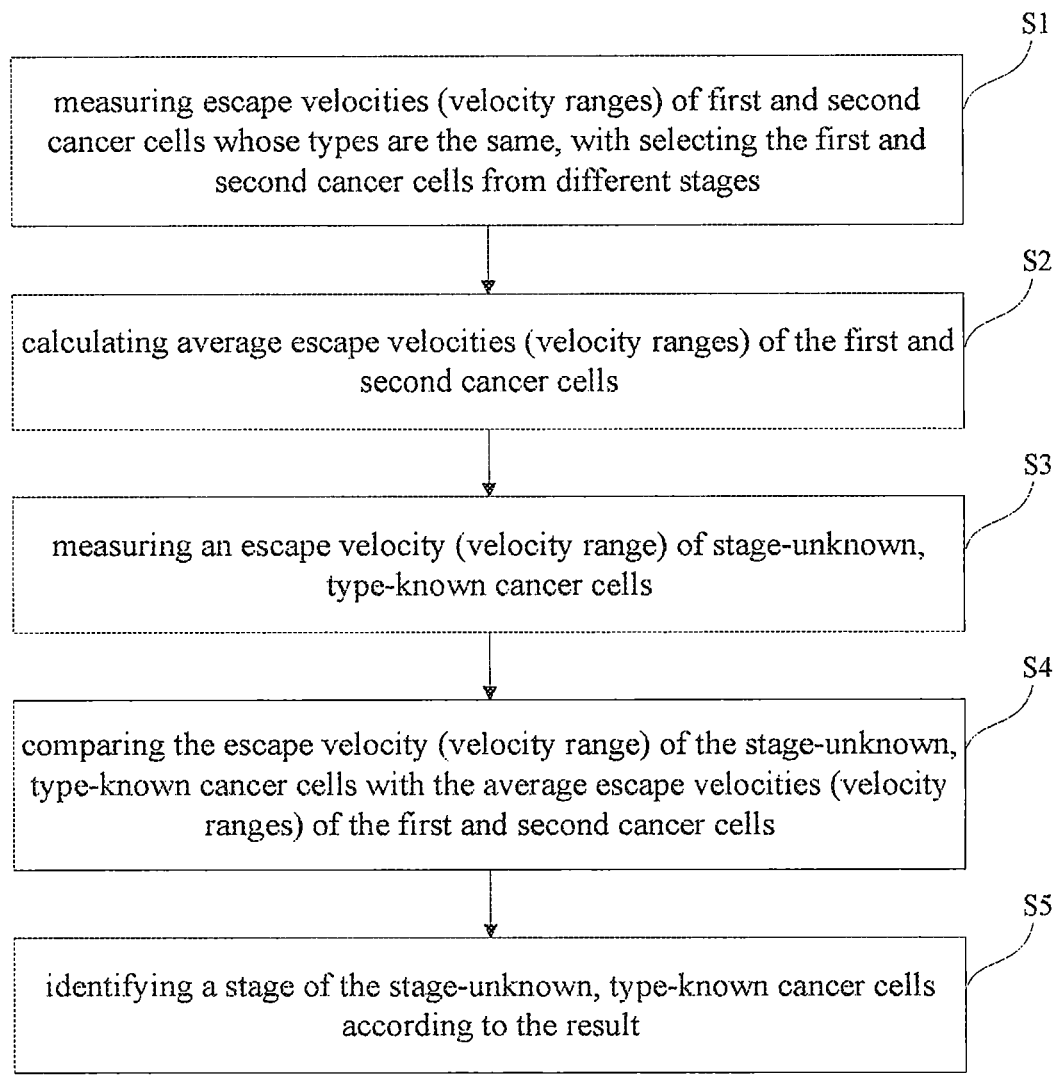
FIG. 2 is a flow chart of the light-trapping cancer cell stage testing method in accordance with the preferred embodiment of the present invention.

FIG. 2 shows a flow chart of the light-trapping cancer cell stage testing method in accordance with the preferred embodiment of the present invention executed by the optical fiber tweezer system shown in FIG. 1. Referring to FIGS. 1 and 2, the light-trapping cancer cell stage testing method of the present invention includes the step S1: utilizing the optical fiber tweezer to measure escape velocities (or velocity ranges) of first cancer cells (e.g. stage II) and second cancer cells (e.g. stage III) whose types are the same, with selecting the first cancer cells and the second cancer cells from different stages. In another embodiment, the escape velocities (or velocity ranges) and the diameters of first cancer cells and second cancer cells are stored in the identification standard database. The escape velocities of first cancer cells and second cancer cells include a maximum escape velocity and a minimum escape velocity.

With continued reference to FIGS. 1 and 2, by way of example, the escape velocities (or velocity ranges) of first cancer cells and second cancer cells are selected from a maximum escape velocity of one cancer cell manipulated by the optical fiber tweezer. With the maximum escape velocity a movement of the operated optical fiber tweezer for such a cancer cell results in falling off the caught cancer cell from it. The escape velocities (or velocity ranges) of the first cancer cells and the second cancer cells are calculated from pathological first-stage escape velocities, pathological second-stage escape velocities, pathological third-stage escape velocities or pathological fourth-stage escape velocities. In a preferred embodiment, the cancer cells are selected from second-stage bladder cancer cells (TSGH-8301), third-stage bladder cancer cells (T24), second-stage colon cancer cells (SW480) and third-stage colon cancer cells (SW620).

With continued reference to FIGS. 1 and 2, the light-trapping cancer cell stage testing method of the present invention includes the step S2: calculating an average escape velocity (or velocity range) or a reference ratio $v_r$ of the escape velocities (or velocity ranges) of the first cancer cells and the second cancer cells by a statistical method. The reference ratio $v_r$ of the escape velocities (or velocity ranges) of the first cancer cells and the second cancer cells is calculated from a range of escape velocities. Advantageously, various average escape velocities $v$ (or velocity ranges) of type-known cancer cells can be used to automatically calculate each reference ratio $v_r$ of the average escape velocities (or velocity ranges). In a preferred embodiment, the identification standard database is used to store the reference ratio $v_r$ of the average escape velocities (or velocity ranges).

With continued reference to FIGS. 1 and 2, the light-trapping cancer cell stage testing method of the present invention includes the step S3: measuring an escape velocity (or velocity range) of stage-unknown cancer cells with a known type by the optical fiber tweezer. In a preferred embodiment, the escape velocity of stage-unknown cancer cells is selected from a maximum or minimum escape velocity.

With continued reference to FIGS. 1 and 2, the light-trapping cancer cell stage testing method of the present invention includes the step S4: comparing the escape velocity (or velocity range) of the stage-unknown, type-known cancer cells with the escape velocities (or velocity ranges) of the first cancer cells and the second cancer cells to obtain a result for cell stage identification.

By way of example, the reference ratio $v_r$ of escape velocities can be calculated by $v_r = v_1/v_2$, where $v_1$ is an escape velocity of stage-known cancer cells and $v_2$ is an average escape velocity of reference-stage cancer cells. A range of the reference ratio $v_r$ of escape velocities of stage-known cancer cells is $$\frac{v_{1(min)}}{v_2} \leq v_r \leq \frac{v_{1(Max)}}{v_2}.$$

With continued reference to FIGS. 1 and 2, the light-trapping cancer cell stage testing method of the present invention includes the step S5: finally, automatically identifying a stage of the stage-unknown, type-known cancer cells according to the result.

By way of example, in identifying a stage of cancer cells, a measured maximum escape velocity $v_{1(max)}$ and a minimum escape velocity $v_{1(min)}$ are calculated with $v_2$ to obtain a range of reference ratio $v_r$. Accordingly, whichever stage of cancer cells can be identified if a calculated value $v_r$ of measured escape velocities of cancer cells is fallen correspondingly within a range of the reference ratio.

Figure 2A:
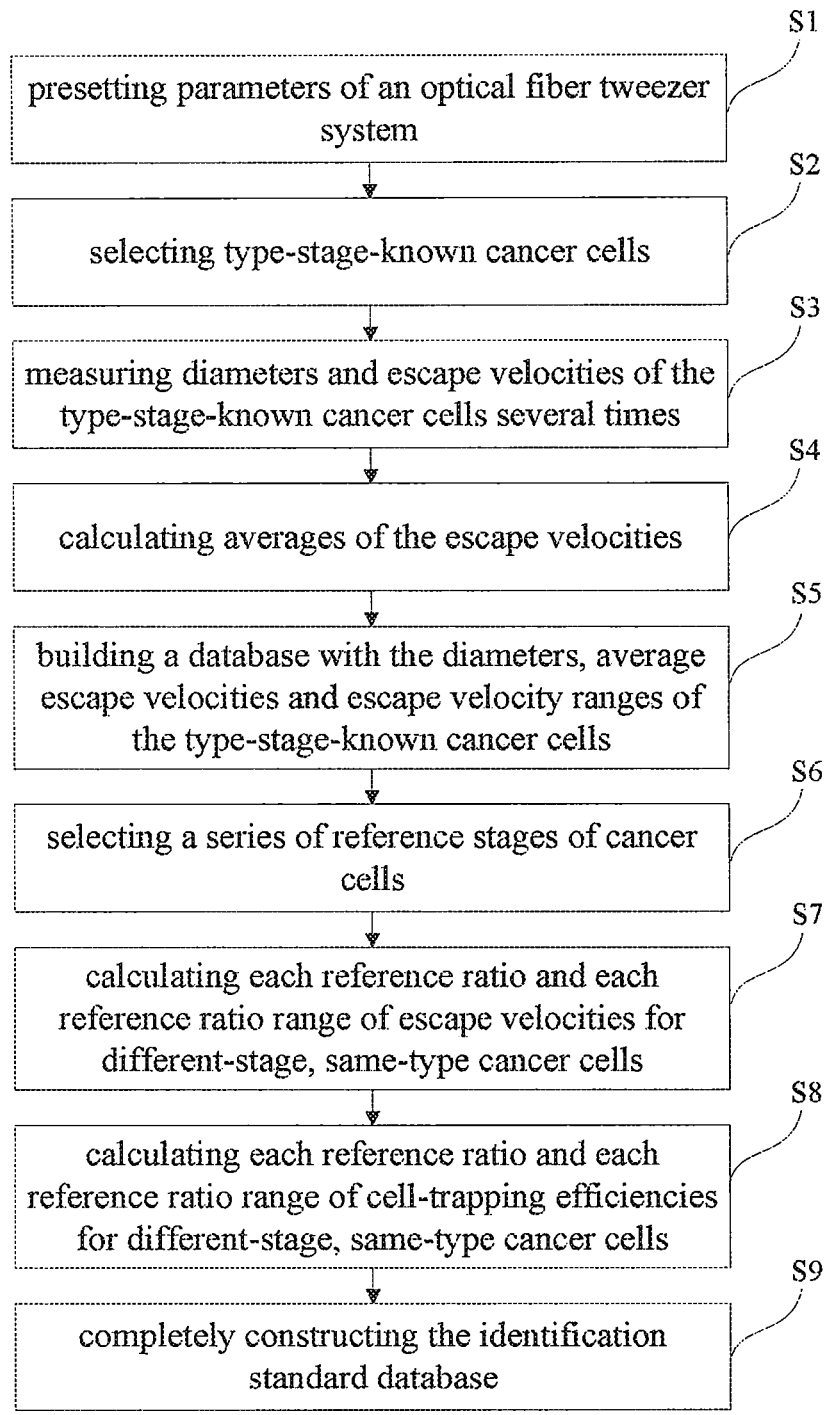
FIG. 2A is a flow chart of a database construction method for testing cancer cell stages in accordance with a preferred embodiment of the present invention.

FIG. 2A shows a flow chart of a database construction method for testing cancer cell stages in accordance with a preferred embodiment of the present invention. Referring to FIGS. 1 and 2A, the database construction method for testing cancer cell stages in accordance with the preferred embodiment of the present invention includes steps: presetting parameters of the optical fiber tweezer system; selecting type-stage-known cancer cells; measuring diameters and escape velocities of the type-stage-known cancer cells (repeatedly) several times; calculating averages of the escape velocities; building an identification standard database with the diameters, average escape velocities and escape velocity ranges of the type-stage-known cancer cells; selecting a series of reference stages of cancer cells; calculating each reference ratio and each reference ratio range of escape velocities for different-stage, same-type cancer cells; calculating each reference ratio and each reference ratio range of cell-trapping efficiencies for different-stage, same-type cancer cells; completely constructing the identification standard database.

Figure 2B:
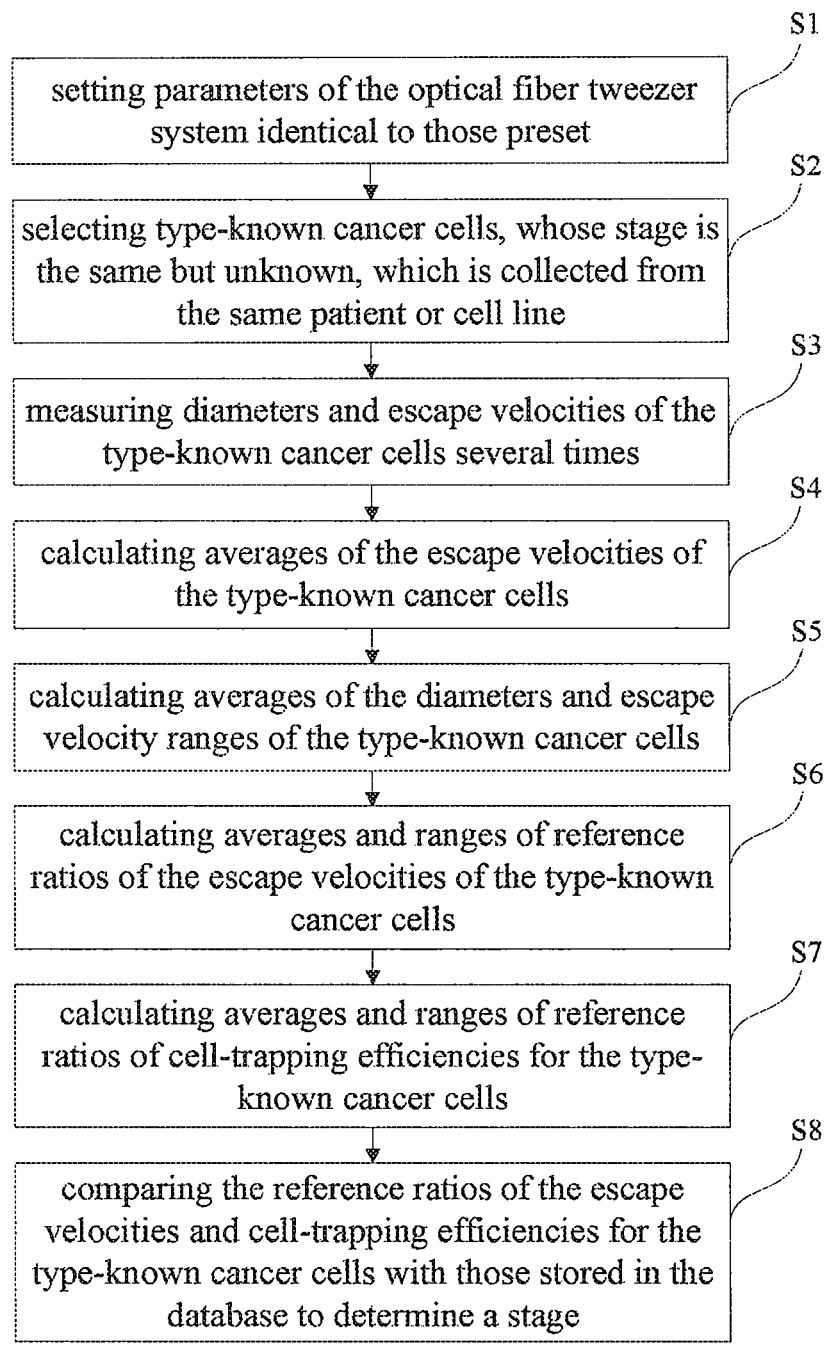
FIG. 2B is a flow chart of a method of testing cancer cell stages in accordance with a preferred embodiment of the present invention.

FIG. 2B shows a flow chart of a method of testing cancer cell stages in accordance with a preferred embodiment of the present invention utilizing the identification standard database shown in FIG. 2A. Referring to FIGS. 1 and 2B, the method of testing cancer cell stages in accordance with the preferred embodiment of the present invention includes steps: setting parameters of the optical fiber tweezer system which is identical to those preset in the database construction method, as shown in FIG. 2A, or stored in the identification standard database; selecting a number of type-known cancer cells, whose stage is the same but unknown, which is collected from the same patient or cell line; measuring diameters and escape velocities of the type-known cancer cells several times, with using the method identical to that shown in the database construction method, as shown in FIG. 2A; calculating averages of the escape velocities of the type-known cancer cells; further calculating averages of the diameters and escape velocity ranges of the type-known cancer cells; calculating averages and ranges of reference ratios of the escape velocities of the type-known cancer cells; calculating averages and ranges of reference ratios of cell-trapping efficiencies for the type-known cancer cells; comparing the reference ratios of the escape velocities and cell-trapping efficiencies for the type-known cancer cells with those stored in the identification standard database to determine a stage of the type-known cancer cells.

Referring again to FIGS. 1 and 2A, in a preferred embodiment, the construction method of the identification standard database includes: utilizing stored diameters r, average escape velocities v and escape velocity ranges to calculate reference ratio $Q_r$ of cell-trapping efficiency. A reference ratio of the cell-trapping efficiency is provided as a range of escape velocity ratio multiplied by diameter ratio. The reference ratio $Q_r$ of the cell-trapping efficiency can be calculated by $$Q_r = \frac{r_1 v_1}{r_s v_2}$$

where $r_1$ is an average diameter of stage-known cancer cells, $r_2$ is an average diameter of reference-stage cancer cells, $v_1$ is an average velocity of stage-known cancer cells and $v_2$ is an average velocity of reference-stage cancer cells. A of reference ratio $Q_r$ of the cell-trapping efficiency for stage-known cancer cells is $$\frac{r_1 v_{1(min)}}{r_2 v_2} \leq Q_r \leq \frac{r_1 v_{1(Max)}}{r_2 v_2}.$$

Referring again to FIGS. 1 and 2B, the cancer cell stage testing method includes: selecting a type of stage-unknown cancer cells (i.e. unidentified cancer cells) to automatically measure several times by an optical fiber tweezer to obtain escape velocities and diameters of the stage-unknown cancer cells.

Referring again to FIGS. 1 and 2B, the cancer cell stage testing method includes: subsequently, calculating an average escape velocity of the stage-unknown cancer cells from the measured escape velocities by a statistical method. The average escape velocity of the stage-unknown cancer cells includes a maximum average escape velocity and a minimum average escape velocity between which to identify an escape velocity of the stage-unknown cancer cells.

Referring again to FIGS. 1 and 2B, the cancer cell stage testing method includes: subsequently, utilizing the calculated average escape velocity of the stage-unknown cancer cells to calculate a range of average escape velocities.

Referring again to FIGS. 1 and 2B, the cancer cell stage testing method includes: subsequently, utilizing the average escape velocities v and the range of escape velocities of the stage-unknown cancer cells to calculate a reference ratio $v_x$ of escape velocities. The reference ratio $v_x$ of escape velocities can be calculated by $$v_x = \frac{v_3}{v_2}$$

where $v_3$ is an escape velocity of the stage-unknown cancer cells and $v_2$ is an average escape velocity of the reference-stage cancer cells.

Referring again to FIGS. 1 and 2B, the cancer cell stage testing method includes: subsequently, utilizing the diameters r, average escape velocities v and escape velocity ranges of the stage-unknown cancer cells to calculate averages and ranges of reference ratios $Q_r$ of the cell-trapping efficiency.

The reference ratios $Q_r$ of cell-trapping efficiency can be calculated by $$Q_x = \frac{r_3 v_3}{r_2 v_2}$$

where $r_3$ is a diameter of the stage-unknown cancer cells and $r_2$ is a diameter of the reference-stage cancer cells, $v_3$ is an escape velocity of the stage-unknown cancer cells and $v_2$ is an average escape velocity of the reference-stage cancer cells.

Referring again to FIGS. 1 and 2B, the cancer cell stage testing method includes: finally, comparing the reference ratios of the escape velocities and the cell-trapping efficiencies for the stage-unknown cancer cells with those of the reference-stage cancer to obtain a result which is used to identify a stage of the stage-unknown cancer cells.

Referring back to FIGS. 1 and 2, by way of example, theoretically the escape velocities of cancer cells may increase as the power of light beam emitted from the optical fiber tweezer increases. Assume that, if the power of light beam is constant, each stage of cancer cells has a specific escape velocity which can be used to identify the stage of cancer cells in testing. Generally, variations of escape velocities of cancer cells (similar stage and same type) with different diameters are non-obvious under the same power conditions of cell-trapping operation. Conversely, variations of escape velocities of the same type of cancer cells with different stages are obviously different under the same power conditions of cell-trapping operation. Different chemical compositions of the cancer cells will result in various escape velocities due to different optical characteristics (e.g., refraction, reflection, transmission or absorption) of the cancer cells.

Generally, the cell-trapping operation of a single-beam optical fiber tweezer can be explained by ray optics. When a light ray travels from one medium into another, it changes speed and momentum of photon which results in refraction as changing direction. The optical fiber tweezer is designed to have such an optical mechanism and is operated to trap tiny particles (i.e. transparent particles) with the light refraction. Namely, when a focused laser beam (light field) emitted from the optical fiber tweezer approaches a targeted cancer cell, a penetrating light ray is refracted in the cancer cell and thus changes its photon momentum to provide an attractive force to trap the cancer cell. As to trapping opaque particles, a double-beam optical fiber tweezer is applied to trap them by a radiation mechanism.

Figure 3:
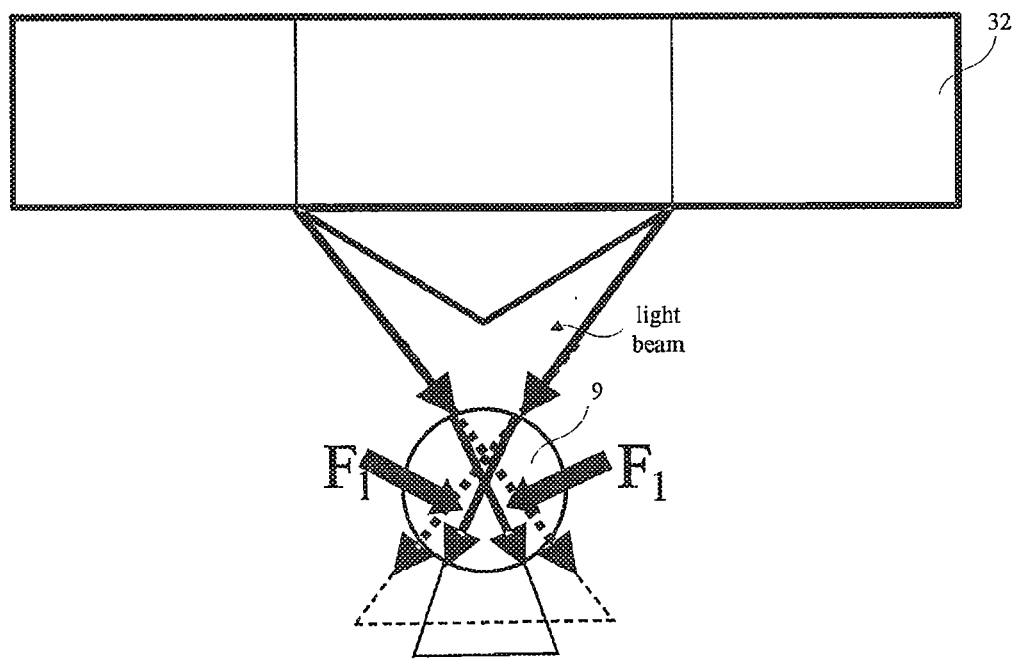
FIG. 3 is a schematic view of an optical fiber tweezer started to catch a cancer cell by the light-trapping cancer cell stage testing method in accordance with the preferred embodiment of the present invention.

FIG. 3 is a schematic view of an optical fiber tweezer started to catch a cancer cell by the light-trapping cancer cell stage testing method in accordance with the preferred embodiment of the present invention. Referring to FIGS. 1 and 3, the light-trapping cancer cell stage testing method includes: utilizing a focused light beam emitted from the optical fiber microlens 32 to trap a cancer cell 9. The optical fiber microlens 32 is provided on a laser optical fiber tweezer system, a 980 nm laser optical fiber tweezer system for example. The optical fiber tweezer has a cell-trapping obliquity or a working distance for cancer cell trapping operation and the cell-trapping obliquity is at 50 degrees. In a preferred embodiment, the optical fiber tweezer includes a single-mode optical fiber or a single-mode optical fiber microlens.

Referring again to FIG. 3, when the light beam emitted from the optical fiber microlens 32 penetrates a surface of the cancer cell 9, it should originally follow a straight line and has not yet changed direction. Subsequently, the incident light beam (shown as two symmetric dotted lines in FIG. 3) is refracted in the cancer cell 9 due to a different refractive index of the vicinity. Namely, interior materials located at two lateral sides of the cancer cell 9 are laterally biased to a longitudinal axis of the optical fiber microlens 32 as if an action force F1 of the interior materials of the cancer cell 9 acts on the incident light beam, as best shown at two symmetrically inward arrows in FIG. 3. The incident light beam is also refracted and deviated from an original path (dotted lines) such that a change of photon momentum is generated.

Figure 4:
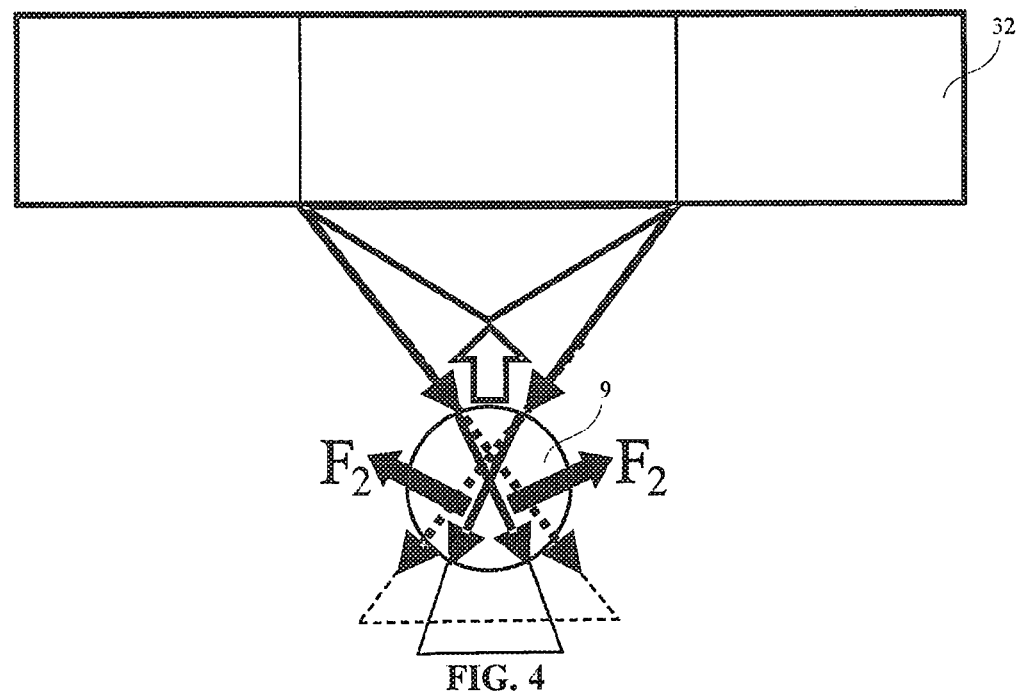
FIG. 4 is a schematic view of the optical fiber tweezer completely operated to catch the cancer cell by the light-trapping cancer cell stage testing method in accordance with the preferred embodiment of the present invention.

FIG. 4 is a schematic view, similar to FIG. 3, of the optical fiber tweezer completely operated to catch the cancer cell by the light-trapping cancer cell stage testing method in accordance with the preferred embodiment of the present invention. Referring to FIGS. 3 and 4, according to Newton's third law of motion, a reaction force F2 of the incident light beam acts on the interior materials located at two lateral sides of the cancer cell 9, as best shown at two symmetrically outward arrows in FIG. 4, with respect to the action force F1. Accordingly, a vertical component of reaction force F2 (shown as vertical arrow in FIG. 4) drives the cancer cell 9 along the longitudinal direction of optical fiber microlens 32. Finally, the (laser) light beam of the optical fiber tweezer is focused by the optical fiber microlens 32 to stably form an optical potential well and to further form a balance point at a focal point to trap the cancer cell 9. As the optical fiber tweezer moves, it may cause a movement of the trapped cancer cell 9. Consequently, the movement of optical fiber tweezer can control that of the trapped cancer cell 9.

Figure 5:
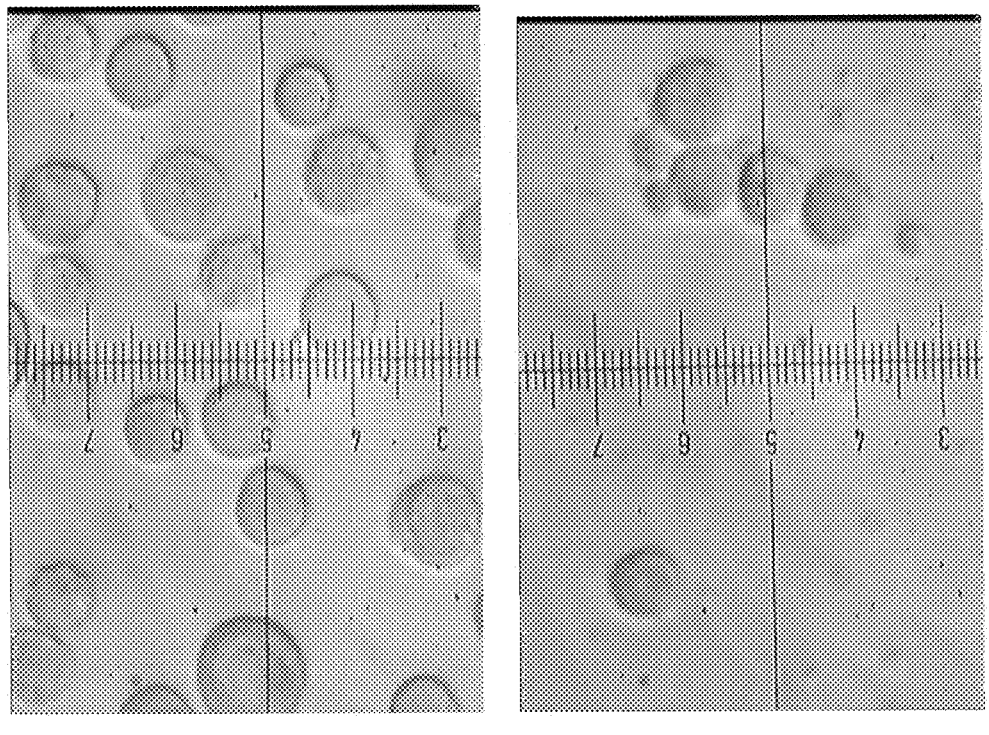
FIG. 5 is a series of microscopic images of second-stage human bladder cancer cells (TSGH-8301) and third-stage human bladder cancer cells (T24) applied in the light-trapping cancer cell stage testing method in accordance with the preferred embodiment of the present invention.
Figure 5:
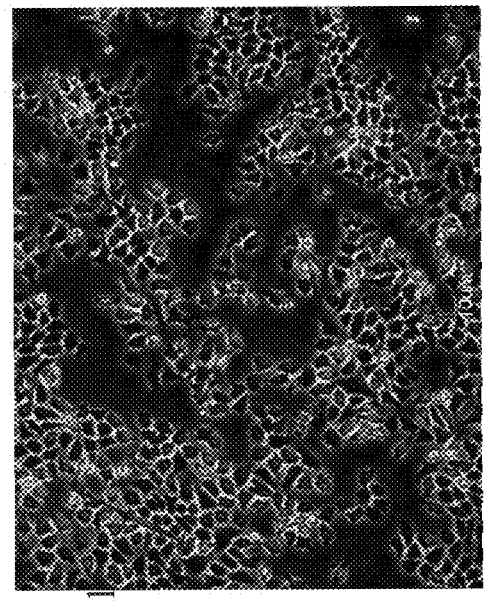
Figure 5:
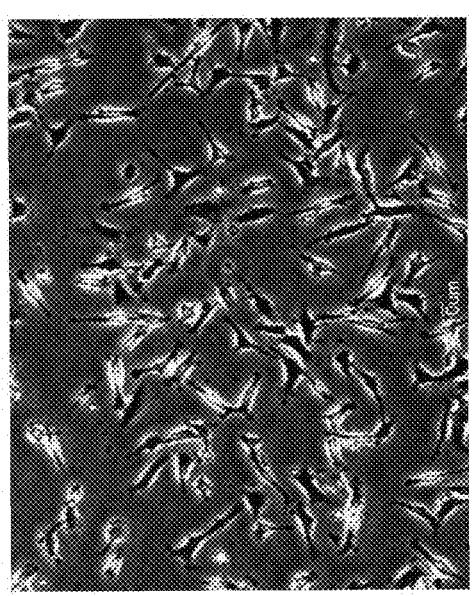

FIG. 5 is a series of microscopic images of second-stage human bladder cancer cells (TSGH-8301) and third-stage human bladder cancer cells (T24) applied in the light-trapping cancer cell stage testing method in accordance with the preferred embodiment of the present invention. The cancer cells are adhered under normal condition, as shown at left portion in FIG. 5, and are suspended after separation treatment, as shown at right portion in FIG. 5. A medium (DMEM) and an optical fiber tweezer with 2.5 mW laser power and one of the two optical fiber microlenses (SMF140303-HV3 and SMF141216-HV3), which correspond to two diameters (15 and 16 μm) and two tapered angles (100° and 102°) respectively, are selected to measure the escape velocities of cancer cells (TSGH-8301 and T24) sequentially as presented in TABLES 1 and 2.

TABLE 1

Diameters and average escape velocities v (average 5 times per cell) of second-stage human bladder cancer cells (TSGH-8301)

| optical fiber microlens | diameter (μm) of microlens | tapered angle of microlens | cancer cell's diameter (μm) | escape velocity v (μm) |
|---|---|---|---|---|
| SMF140303-HV3 | 16 | 100° | 16 | 5.92 |
|  |  |  | 15 | 6.43 |
|  |  |  | 15 | 5.02 |
|  |  |  | 14 | 6.31 |
| SMF141216-HV3 | 15 | 102° | 15 | 6.31 |
|  |  |  | 16 | 5.92 |
|  |  |  | 17 | 5.66 |
|  |  |  | 15 | 6.18 |
|  |  |  | 13 | 6.31 |
|  |  |  | 16 | 6.05 |

TABLE 2

Diameters and average escape velocities v (average 5 times per cell) of third-stage human bladder cancer cells (T24)

| optical fiber microlens | diameter (μm) of microlens | tapered angle of microlens | cancer cell's diameter (μm) | escape velocity v (μm) |
|---|---|---|---|---|
| SMF140303-HV3 | 16 | 100° | 16 | 3.99 |
|  |  |  | 17 | 3.74 |
|  |  |  | 16 | 4.12 |
|  |  |  | 14 | 4.38 |
|  |  |  | 14 | 4.51 |
| SMF141216-HV3 | 15 | 102° | 15 | 3.99 |
|  |  |  | 16 | 3.61 |
|  |  |  | 13 | 3.86 |
|  |  |  | 14 | 3.86 |
|  |  |  | 13 | 4.12 |

Figure 6:
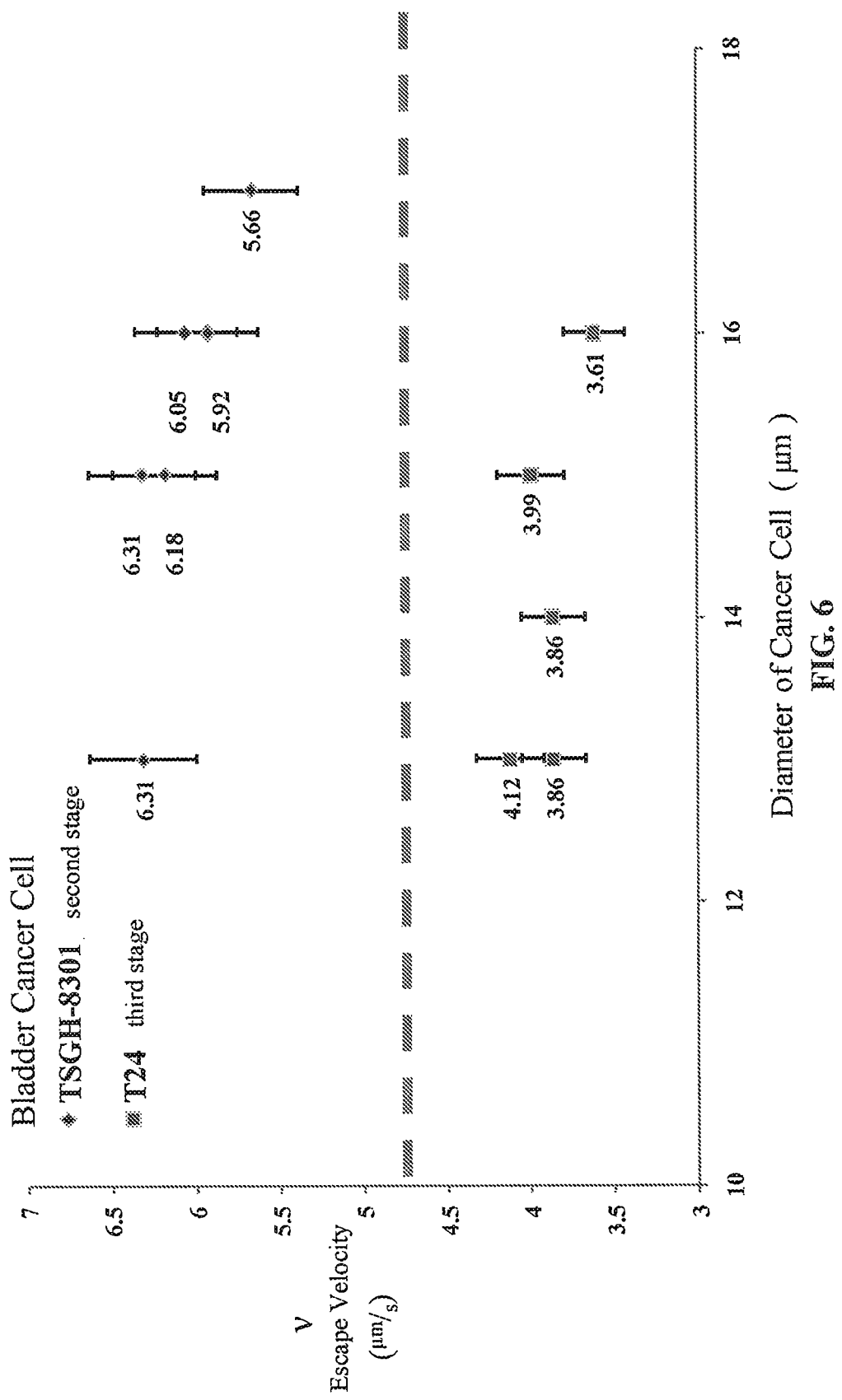
FIG. 6 is a chart illustrating diameters of the second-stage human bladder cancer cells (TSGH-8301) and the third-stage human bladder cancer cells (T24) in relation to escape velocities measured by the light-trapping cancer cell stage testing method in accordance with the preferred embodiment of the present invention.

FIG. 6 is a chart illustrating diameters of the second-stage human bladder cancer cells (TSGH-8301), as shown in upper portion in FIG. 6, and the third-stage human bladder cancer cells (T24), as shown in lower portion in FIG. 6, in relation to escape velocities (average escape velocity, maximum and minimum escape velocity) measured by the light-trapping cancer cell stage testing method in accordance with the preferred embodiment of the present invention. Referring to FIG. 6, variations of the maximum escape velocities of the same-stage cancer cells are non-obvious. A maximum escape velocity $v_1$ of the stage-unknown cancer cells is measured with respect to an average maximum escape velocity $v_2$ of the third-stage cancer cells. A ratio $v_r$ of escape velocities is calculated by the maximum escape velocity $v_1$ divided by the average maximum escape velocity $v_2$. The average maximum escape velocity $v_2$ is an average value calculated from all of the measured escape velocities of the same-stage cancer cells.

With continued reference to FIG. 6, after calculating the ratio of escape velocities, two ranges of the reference ratio $v_r$ of second-stage human bladder cancer cells (TSGH-8301) and third-stage human bladder cancer cells (T24) are $1.46 \leq v_r \leq 1.62$ and $0.93 \leq v_r \leq 1.06$, respectively. Suppose an escape velocity $v_3$ of the stage-unknown is measured and calculated with the escape velocity $v_1$ or $v_2$ to obtain a ratio $v_x$. A stage of the cancer cell can be determined as second stage or third stage if the ratio $v_x$ is fallen within one range of the above reference ratio $v_r$.

Figure 7:
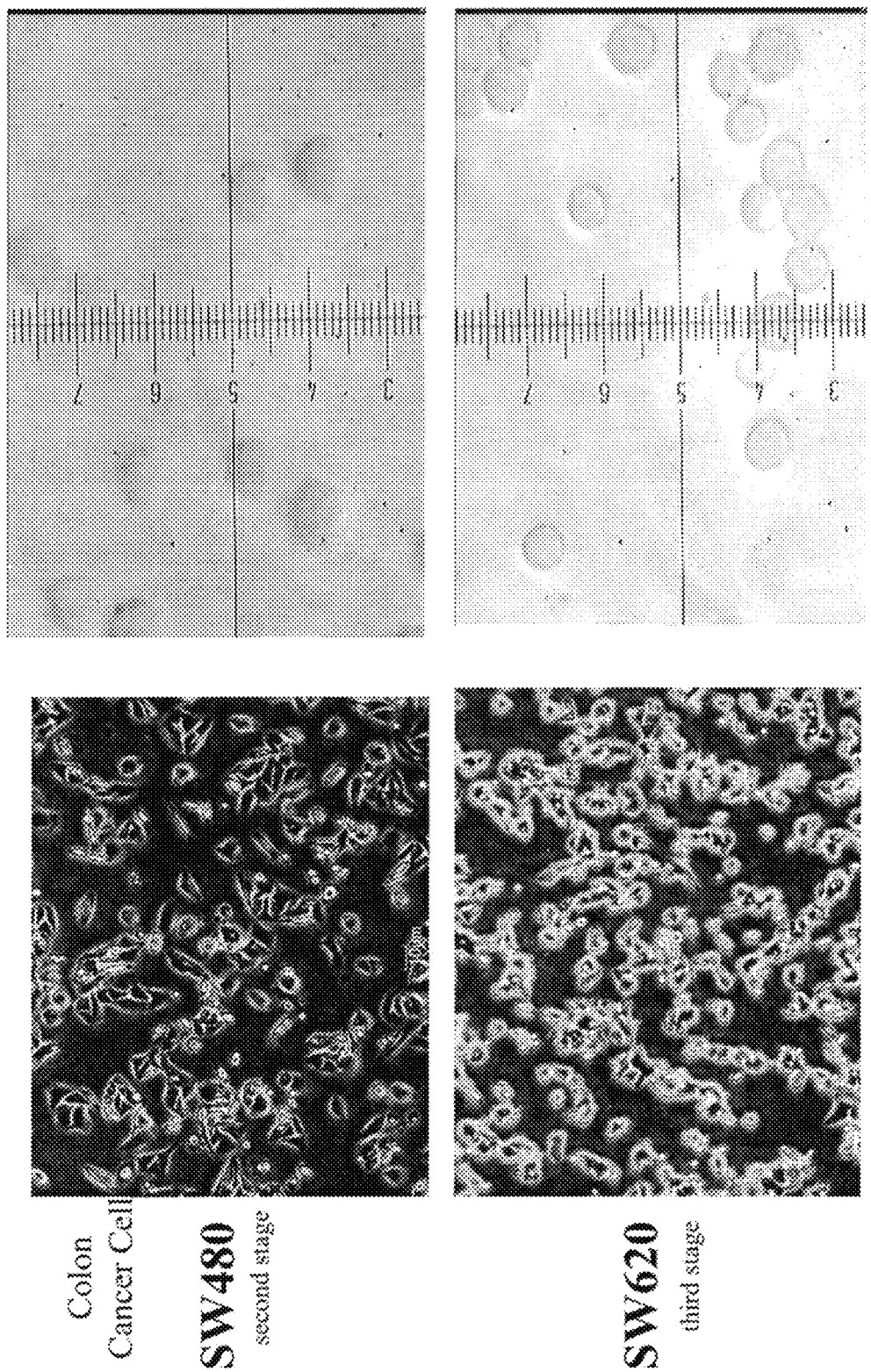
FIG. 7 is a series of microscopic images of second-stage human colon cancer cells (SW480) and third-stage human colon cancer cells (SW620) applied in the light-trapping cancer cell stage testing method in accordance with the preferred embodiment of the present invention.

FIG. 7 is a series of microscopic images of second-stage human colon cancer cells (SW480) and third-stage human colon cancer cells (SW620) applied in the light-trapping cancer cell stage testing method in accordance with the preferred embodiment of the present invention. The suspended cancer cells (SW480) and (SW620) are selected for cell stage testing. A medium (L15) and an optical fiber tweezer with 2.5 mW laser power and an optical fiber microlens (SMF141216-HV3), which corresponds to a diameter (15 μm) and a tapered angle (102°), are selected to measure the escape velocities of cancer cells (SW480 and SW620) sequentially as presented in TABLES 3 and 4.

TABLE 3

Diameters and average escape velocities v (average 5 times per cell) of second-stage human colon cancer cells (SW480)

| optical fiber microlens | diameter (μm) of microlens | tapered angle of microlens | cancer cell's diameter (μm) | escape velocity v (μm) |
|---|---|---|---|---|
| SMF141216-HV3 | 15 | 102° | 13 | 7.21 |
|  |  |  | 15 | 6.56 |
|  |  |  | 15 | 6.82 |
|  |  |  | 14 | 7.08 |
|  |  |  | 14 | 6.82 |
|  |  |  | 13 | 7.33 |

TABLE 4

Diameters and average escape velocities v (average 5 times per cell) of third-stage human colon cancer cells (SW620)

| optical liber microlens | diameter (μm) of microlens | tapered angle of microlens | cancer cells diameter (μm) | escape velocity v (μm) |
|---|---|---|---|---|
| SMF141216-HV3 | 15 | 102° | 15 | 4.25 |
|  |  |  | 14 | 4.51 |
|  |  |  | 13 | 4.64 |
|  |  |  | 13 | 4.51 |
|  |  |  | 12 | 4.76 |
|  |  |  | 14 | 4.25 |

Figure 8:
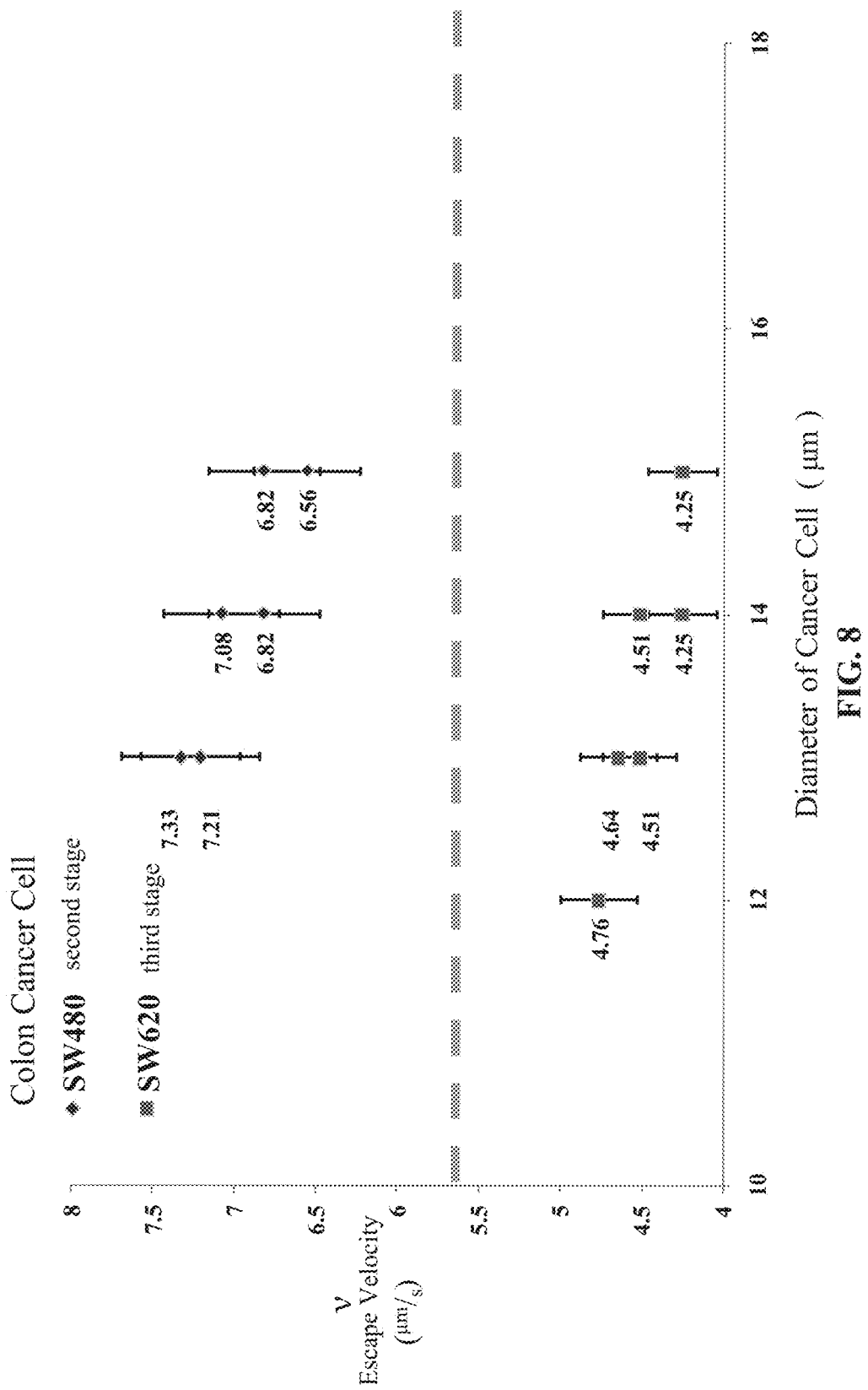
FIG. 8 is a chart illustrating diameters of the second-stage human colon cancer cells (SW480) and the third-stage human colon cancer cells (SW620) in relation to escape velocities measured by the light-trapping cancer cell stage testing method in accordance with the preferred embodiment of the present invention.

FIG. 8 is a chart illustrating diameters of the second-stage human colon cancer cells (SW480), as shown in upper portion in FIG. 8, and the third-stage human colon cancer cells (SW620), as shown in lower portion in FIG. 8, in relation to escape velocities measured by the light-trapping cancer cell stage testing method in accordance with the preferred embodiment of the present invention. Referring to FIG. 8, after calculating the ratio of escape velocities, two ranges of the reference ratio $v_r$ of second-stage human colon cancer cells (SW480) and third-stage human colon cancer cells (SW620) are $1.46 \leq v_r \leq 1.63$ and $0.95 \leq v_r \leq 1.06$, respectively. Suppose an escape velocity $v_3$ of the stage-unknown is measured and calculated with the escape velocity $v_1$ or $v_2$ to obtain a ratio $v_x$. A stage of the cancer cell can be determined as second stage or third stage if the ratio $v_x$ is fallen within one range of the above reference ratio $v_r$.

Although the invention has been described in detail with reference to its presently preferred embodiment, it will be understood by one of ordinary skills in the art that various modifications can be made without departing from the spirit and the scope of the invention, as set forth in the appended claims.

What is claimed is:

1. A light-trapping cancer cell stage testing method comprising:
    a) utilizing an optical fiber tweezer to measure escape velocities of first cancer cells and second cancer cells whose types are the same, with selecting the first cancer cells and the second cancer cells from different stages;
    b) calculating average escape velocities of the first cancer cells and the second cancer cells;
    c) measuring at least one escape velocity of stage-unknown, same type of cancer cells using the optical fiber tweezer;
    d) comparing the at least one escape velocity of the stage-unknown, same type of cancer cells with the average escape velocities of the first cancer cells and the second cancer cells to obtain a result; and
    e) identifying a stage of the stage-unknown, same type of cancer cells according to the result.

2. The method as defined in claim 1, wherein the escape velocities of the first cancer cells and the second cancer cells include maximum escape velocities and minimum escape velocities.

3. The method as defined in claim 1, wherein the average escape velocities of the first cancer cells and the second cancer cells are calculated from pathological first-stage escape velocities, pathological second-stage escape velocities, pathological third-stage escape velocities or pathological fourth-stage escape velocities.

4. The method as defined in claim 1, wherein the escape velocities of the first cancer cells and the second cancer cells are calculated to provide a reference ratio of escape velocity or cell-trapping efficiency.

5. The method as defined in claim 1, wherein the escape velocity of the stage-unknown, same type of cancer cells is a maximum escape velocity or a minimum escape velocity.

6. The method as defined in claim 1, wherein the stage-unknown, same type of cancer cells are human bladder cancer cells.

7. The method as defined in claim 1, wherein the stage-unknown, same type of cancer cells are human colon cancer cells.

8. The method as defined in claim 1, wherein the optical fiber tweezer is a laser optical fiber tweezer.

9. The method as defined in claim 1, wherein the optical fiber tweezer has a cell-trapping obliquity or a working distance.

10. The method as defined in claim 1, wherein the optical fiber tweezer includes a single-mode optical fiber or a single-mode optical fiber microlens.

11. A light-trapping cancer cell stage testing method comprising:
   a) utilizing an optical fiber tweezer to measure escape velocity ranges of first cancer cells and second cancer cells whose types are the same, with selecting the first cancer cells and the second cancer cells from different stages;
   b) calculating average escape velocity ranges of the first cancer cells and the second cancer cells;
   c) measuring at least one escape velocity range of stage-unknown, same type of cancer cells using the optical fiber tweezer;
   d) comparing the at least one escape velocity range of the stage-unknown, same type of cancer cells with the average escape velocity ranges of the first cancer cells and the second cancer cells to obtain a result; and
   e) identifying a stage of the stage-unknown, same type of cancer cells according to the result.

12. The method as defined in claim 11, wherein the escape velocity ranges of the first cancer cells and the second cancer cells calculated from maximum escape velocities and minimum escape velocities.

13. The method as defined in claim 11, wherein the average escape velocity ranges of the first cancer cells and the second cancer cells are calculated from pathological first-stage escape velocity ranges, pathological second-stage escape velocity ranges, pathological third-stage escape velocity ranges or pathological fourth-stage escape velocity ranges.

14. The method as defined in claim 11, wherein the escape velocity ranges of the first cancer cells and the second cancer cells are calculated to provide a reference ratio of escape velocity or cell-trapping efficiency.

15. The method as defined in claim 11, wherein the escape velocity range of the stage-unknown, same type of cancer cells is calculated from a maximum escape velocity and a minimum escape velocity.

16. The method as defined in claim 11, wherein the stage-unknown, same type of cancer cells are human bladder cancer cells.

17. The method as defined in claim 11, wherein the stage-unknown, same type of cancer cells are human colon cancer cells.

18. The method as defined in claim 11, wherein the optical fiber tweezer is a laser optical fiber tweezer.

19. The method as defined in claim 11, wherein the optical fiber tweezer has a cell-trapping obliquity or a working distance.

20. The method as defined in claim 11, wherein the optical fiber tweezer includes a single-mode optical fiber or a single-mode optical fiber microlens.

* * * * *